(12) United States Patent
Benderly et al.

(10) Patent No.: US 8,049,036 B2
(45) Date of Patent: Nov. 1, 2011

(54) MULTI-STAGED CATALYST SYSTEMS AND PROCESS FOR CONVERTING ALKANES TO ALKENES AND TO THEIR CORRESPONDING OXYGENATED PRODUCTS

(75) Inventors: Abraham Benderly, Elkins Park, PA (US); Anne Mae Gaffney, West Chester, PA (US); Mark Anthony Silvano, New Hope, PA (US)

(73) Assignee: Rohm and Haas Company, Philadelphia, PA (US)

( * ) Notice: Subject to any disclaimer, the term of this patent is extended or adjusted under 35 U.S.C. 154(b) by 834 days.

(21) Appl. No.: 12/009,556

(22) Filed: Jan. 18, 2008

(65) Prior Publication Data

US 2011/0105784 A1      May 5, 2011

Related U.S. Application Data

(62) Division of application No. 11/269,434, filed on Nov. 8, 2005, now Pat. No. 7,361,622.

(60) Provisional application No. 60/629,989, filed on Nov. 22, 2004.

(51) Int. Cl.
*C07C 53/00* (2006.01)

(52) U.S. Cl. ........ 562/512; 562/409; 560/129; 560/205; 560/211; 585/324; 502/117; 502/300; 502/311; 502/328

(58) Field of Classification Search .................. None
See application file for complete search history.

(56) References Cited

U.S. PATENT DOCUMENTS

| | | | |
|---|---|---|---|
| 3,649,930 A | | 3/1972 | Le Floch |
| 3,692,701 A | * | 9/1972 | Box .............................. 502/329 |
| 3,825,600 A | | 7/1974 | Ohara et al. |
| 4,339,355 A | | 7/1982 | Decker et al. |
| 5,705,684 A | * | 1/1998 | Hefner et al. .................. 562/545 |
| 6,809,219 B2 | * | 10/2004 | Han et al. ....................... 562/549 |

FOREIGN PATENT DOCUMENTS

| | | |
|---|---|---|
| JP | 6199731 A | 1/1993 |
| JP | 06199731 | 7/1994 |

\* cited by examiner

*Primary Examiner* — Sudhakar Katakam
(74) *Attorney, Agent, or Firm* — Marcella M. Bodner

(57) ABSTRACT

Alkenes, unsaturated saturated carboxylic acids, saturated carboxylic acids and their higher analogues are prepared cumulatively from corresponding alkanes utilizing using a multi-staged catalyst system and a multi-stage process which comprises steam cracking of alkanes to corresponding alkenes at flame temperatures and at short contact times in combination with one or more oxidation catalysts for catalytically converting the corresponding alkenes to further corresponding oxygenated products using short contact time reactor conditions.

3 Claims, No Drawings

MULTI-STAGED CATALYST SYSTEMS AND PROCESS FOR CONVERTING ALKANES TO ALKENES AND TO THEIR CORRESPONDING OXYGENATED PRODUCTS

CROSS REFERENCE TO RELATED PATENT APPLICATIONS

This non-provisional application is a divisional of non-provisional U.S. patent application Ser. No. 11/269,434 filed Nov. 8, 2005, now U.S. Pat. No. 7,361,622, benefit of which is claimed under 35 U.S.C. §120 and which in turn claims benefit under 35 U.S.C. §119(e) of U.S. provisional Application No. 60/629,989 filed Nov. 22, 2004, priority benefit of which is also claimed for the present divisional application.

The present invention relates to alkane oxidation/dehydrogenation catalysts and processes for converting alkanes and oxygen to dehydrogenated products and/or oxygenated products at flame temperatures. More particularly, the present invention is directed to a multi-staged process which includes but is not limited to converting alkanes to corresponding alkenes by steam cracking followed by converting alkenes to the corresponding oxygenated products under short contact time reactor conditions. In addition, the present invention is directed to catalyst systems for converting specific alkanes to their corresponding alkenes and oxygenates including unsaturated carboxylic acids, saturated carboxylic acids, esters of unsaturated carboxylic acids and their respective higher analogues in a short contact time reactor at flame temperatures; to a method for making the catalyst systems; and to a hybrid process for the gas phase catalytic oxidation of alkanes using the catalyst systems. The invention is also directed to catalyst systems for converting saturated carboxylic acids to their corresponding unsaturated carboxylic acids and to higher analogue esters of unsaturated carboxylic acids and to a multi-staged process for the gas phase catalytic oxidation of saturated carboxylic acids. The invention is also directed to a multi-staged process for the gas phase oxidation of alkanes that includes the staging of additional feeds including alkenes, oxygen, formaldehyde and alcohols for preparing unsaturated carboxylic acids, esters of unsaturated carboxylic acids and their respective higher analogues using the catalyst systems.

The selective partial oxidation of alkenes to unsaturated carboxylic acids and their corresponding esters is an important commercial process. However, the selective partial oxidation/dehydrogenation of alkanes to products including olefins, unsaturated carboxylic acids and esters of unsaturated carboxylic acids is an important industrial problem with a number of challenges to overcome. One limitation of short contact time oxidative dehydrogenation of alkanes concerns the first step, namely the low yields associated with converting alkanes to their corresponding alkenes due to several competing reactions, including but not limited to for example, over oxidation which leads to CO, $CO_2$, water, alkane fragments (Cn-m) and alkene fragments (C2n-m). The relatively low selectivity of using mixed metal oxide catalysts to convert alkanes to their corresponding alkenes under short contact time reactor conditions is due to several factors including, but not limited to for example, the following: (a) the catalyst generating flame temperature conditions also tends to catalyze over oxidation reactions of the alkanes and corresponding alkenes; (b) relatively low alkanes/oxygen ratios, needed to sustain the flame temperature conditions, which also tends to catalyze over oxidation reactions of the alkanes and corresponding alkenes; (c) the overall reaction kinetics favor oxidation of alkanes to CO and carbon dioxide over desired oxidative dehydrogenation products, including corresponding alkenes.

U.S. Pat. No. 5,705,684 describes a process for preparing acrolein and acrylic acid from propane using different multi-metal oxide catalysts in stages. In a first stage, propane is dehydrogenated with a Mo—Bi—Fe oxide catalyst to propylene, which is used in a second stage as a feed to an oxidation reactor containing a Mo—V oxide catalyst and contacted with oxygen to produce a mixture of acrolein and acrylic acid. However, the endothermic process requires a costly removal of hydrogen in the first stage, rendering the process prohibitive on a commercial scale. In addition, at flame temperatures the Mo—Bi—Fe oxide catalyst described is thermally unstable. Inventors have discovered a unique, efficient and commercially feasible multi-staged solution for converting specific alkanes to their corresponding alkenes and oxygenated products including unsaturated carboxylic acids, saturated carboxylic acids and esters of unsaturated carboxylic acids using novel catalyst systems at flame temperatures in a short contact time reactor combined with a steam cracking of corresponding alkanes as the initial step. In addition, catalysts for converting saturated carboxylic acids to their corresponding unsaturated carboxylic acids and to higher analogue esters of unsaturated carboxylic acids at flame temperatures in a short contact time reactor and using the multi-staged method have been discovered. To improve the overall yields and selectivities of catalytically converting alkanes to corresponding alkenes, inventors have discovered a multi-staged process that includes steam cracking of alkanes followed by reacting correspondingly produced alkenes to further corresponding oxygenated products under short contact time reactor conditions. In another multi-staged process, for example, small amounts of corresponding alkanes are reacted with stoichiometric amounts of oxygen sufficient for total oxidation to carbon dioxide and water. The hot gaseous stream of carbon dioxide and steam is directed into a cracking zone, including a conventional cracking catalyst known in the art. The heated steam has duel purposes to heat the cracking catalyst bed and to provide steam for the cracking process. The remaining major amounts of corresponding alkanes will be combined with the carbon dioxide steam mixture under turbulent flow conditions. The mixture of gases are then directed to contact the cracking catalyst to provide corresponding alkenes in higher yields and selectivities. The converted corresponding alkenes are then further catalytically converted to corresponding oxygenates under short contact time reactor conditions. In another multi-staged process, for example, alkenes produced from dehydrogenation of alkanes using such catalysts are deliberately produced as in-process chemical intermediates by steam cracking and not isolated before selective partial oxidation to oxygenated products.

Several advantages of the present invention include but are not limited to for example a lowered capital investment based upon reduced reactor size, energy savings due to the sacrificial alkane burning for light off and heat generation, eliminates the need for an additional steam integration step since the multi-staged method generates its own steam in the first phase (cracking step), readily achieves the thermodynamic limits of alkene production with minimal catalyst investment and maintenance.

Accordingly, the present invention provides a multi-stage catalyst system comprising: at least one cracking catalyst for converting alkanes to their corresponding alkenes at flame temperatures and at short contact times and at least one oxidation catalyst for further converting corresponding alkenes to their corresponding oxygenated products including, but not limited to for example, saturated carboxylic acids and unsaturated carboxylic acids at flame temperatures and at short contact times, the at least one oxidation catalyst comprising: (a) at least one metal selected from the group consisting of Ag, Au, Ir, Ni, Pd, Pt, Rh, Ru, alloys thereof and combinations thereof; and (b) at least one modifier selected from the group of metal oxides including the metals Bi, In, Mg, P, Sb, Zr, Group 1-3 metals, lanthanide metals and combinations thereof, in combination with or without (c) at least one metal oxide including the metals Cd, Co, Cr, Cu, Fe, Mn, Ni, Nb, Ta, V, Zn, binary combinations thereof, ternary combinations thereof and higher combinations thereof; wherein the catalysts are impregnated on a metal oxide support.

According to a separate embodiment the multi-staged catalyst system includes an additional catalyst for converting saturated carboxylic acids to their corresponding unsaturated carboxylic acids at short contact times comprising: at least one metal oxide including the metals Mo, Fe, P, V and combinations thereof.

The invention provides a multi-staged catalyst bed for cumulatively converting alkanes to their corresponding alkenes saturated carboxylic acids and unsaturated carboxylic acids comprising: (a) a first catalyst layer comprising: at least one steam cracking catalyst at flame temperatures and at short contact times; (b) a second catalyst layer further comprising: (i) at least one metal selected from the group consisting of Ag, Au, Ir, Ni, Pd, Pt, Rh, Ru, alloys thereof and combinations thereof; and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts of the first layer are impregnated on a metal oxide support; and (c) a third catalyst layer comprising at least one metal oxide including the metals Mo, Fe, P, V and combinations thereof, wherein the catalyst of the third layer is impregnated on a metal oxide support and is oriented downstream from the second catalyst layer and is oriented further downstream from the first catalyst layer to increase the overall yield of unsaturated carboxylic acid from its corresponding alkane.

According to a separate embodiment, the catalyst bed includes an additional catalyst layer for converting saturated carboxylic acids to their corresponding higher analogue unsaturated carboxylic acids and esters of unsaturated carboxylic acids at short contact times comprising: at least one metal oxide including the metals V, Nb, Ta and combinations thereof. The invention provides a multi-staged catalyst bed for cumulatively converting alkenes to their corresponding unsaturated carboxylic acids, esters of unsaturated carboxylic acids and their respective higher analogues comprising comprising:
(a) a first catalyst layer comprising: at least one steam cracking catalyst at flame temperatures and at short contact times;
(b) a second catalyst layer further comprising: (i) at least one metal selected from the group consisting of Ag, Au, Ir, Ni, Pd, Pt, Rh, Ru, alloys thereof and combinations thereof, and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, the first catalyst layer cumulatively effective for converting the alkene to its corresponding saturated carboxylic acid and unsaturated carboxylic acid wherein the catalysts of the first layer are impregnated on a metal oxide support; and
(c) a third catalyst layer cumulatively effective for converting the saturated carboxylic acid and unsaturated carboxylic acid to its corresponding saturated higher analogue unsaturated carboxylic in the presence of an aldehyde, its corresponding ester of an unsaturated carboxylic acid in the presence of an alcohol and its corresponding higher analogue ester of an unsaturated carboxylic acid in the presence of both formaldehyde and an alcohol.

According to one embodiment the second catalyst layer comprises one or more superacids and is self supporting or optionally impregnated on a metal oxide support and is oriented downstream from the second catalyst layer to increase the overall yield of corresponding ester of an unsaturated carboxylic acid, higher analogue unsaturated carboxylic acid and ester thereof.

According to one embodiment, additional feeds are incorporated (also referred to a staging) including alkenes, oxygen, formaldehyde and alcohols for preparing unsaturated carboxylic acids, esters of unsaturated carboxylic acids and their respective higher analogues using the catalyst system. Staging formaldehyde between the two catalyst layers produces the corresponding higher analogue unsaturated carboxylic acid ($C_n+C_1$). For example, the first catalyst converts propane ($C_3$ alkane) to propionic acid ($C_3$ saturated carboxylic acid) and the second catalyst converts propionic acid to a higher analogue methacrylic acid ($C_4$ unsaturated carboxylic acid) in the presence of formaldehyde.

According to a separate embodiment, sparging formaldehyde and staging an alcohol between the two catalyst beds produces the corresponding higher analogue ester of unsaturated carboxylic acid. For example, the first catalyst converts propane ($C_3$) to propionic acid ($C_3$) and the second catalyst converts propionic acid ($C_3$) to methyl methacrylate ($C_4$) in the presence of formaldehyde and methanol.

The invention provides a multi-stage method for preparing alkenes from corresponding alkanes, the process comprising the steps of:
(a) combining 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more stem cracking catalysts;
(c) combining the gaseous mixture generated from (b) and molecular oxygen to a short contact time reactor, the reactor including a catalyst system comprising (a) at least one metal selected from the group consisting of Ag, Au, Ir, Ni, Pd, Pt, Rh, Ru, alloys thereof and combinations thereof; and (b) at least one modifier selected from the group of metal oxides including the metals Bi, In, Mg, P, Sb, Zr, Group 1-3 metals, lanthanide metals and combinations thereof, the catalyst system cumulatively effective at converting the gaseous alkane to its corresponding gaseous alkene;
wherein the reactor is operated at a temperature of from 700° C. to 1000° C., with a reactor residence time of no greater than 100 milliseconds.

The invention provides a multi-stage process for preparing unsaturated carboxylic acids from corresponding alkanes, the process comprising the steps of:

(a) passing 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more steam cracking catalysts; and
(c) catalytically converting the corresponding alkene generated from (b) and molecular oxygen to a short contact time reactor, the reactor including a mixed catalyst bed comprising (1) a first catalyst layer comprising (i) at least one metal selected from the group consisting of Ag, Au, Ir, Ni, Pd, Pt, Rh, Ru, alloys thereof and combinations thereof; and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts of the first layer are impregnated on a metal oxide support; and (2) a second catalyst layer comprising at least one metal oxide including the metals Mo, Fe, P, V and combinations thereof, the mixed bed catalyst cumulatively effective at converting the gaseous alkene to its corresponding gaseous unsaturated carboxylic acid;

wherein the second catalyst layer is separated at a distance downstream from the first catalyst layer and the reactor is operated at a temperature of from 500° C. to 1000° C., with a reactor residence time of no greater than 100 milliseconds; and wherein the one or more cracking catalysts is separated at a distance upstream from the short contact time reactor.

As a separate embodiment, the present invention provides a multi-stage process for preparing unsaturated carboxylic acids from corresponding alkanes, the process comprising the steps of
(a) passing 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more steam cracking catalysts;
(c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof, and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid; and
(d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid;
wherein the one or more cracking catalysts is separated at a distance upstream relative to the direction of flow of the gaseous stream to the first and second catalyst zones comprising the short contact time reactor;
the first catalyst zone being disposed upstream of the second catalyst zone relative to the direction of flow of the gaseous stream through the reactor;
the first catalyst zone being operated at a temperature of from 500° C. to 1000° C., with a first reaction zone residence time of no greater than 100 milliseconds;
the second catalyst zone being operated at a temperature of from 300° C. to 400° C., with a second reaction zone residence time of no greater than 100 milliseconds;
wherein the gaseous stream of the alkene is passed through the reactor in a single pass or wherein any unreacted alkene is recycled back into the gaseous stream of alkene entering the reactor and wherein any saturated carboxylic acid is recycled back into the second catalyst zone to increase the overall yield of unsaturated carboxylic acid.

The invention also provides a multi-stage process for converting alkanes to their corresponding esters of unsaturated carboxylic acids, the process comprising the steps of:
(a) passing 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more steam cracking catalysts; and
(c) catalytically converting the corresponding alkene generated from (b) and molecular oxygen to a short contact time reactor, the reactor including a mixed catalyst bed comprising (1) a first catalyst layer comprising (i) at least one metal selected from the group consisting of Ag, Au, Ir, Ni, Pd, Pt, Rh, Ru, alloys thereof and combinations thereof; and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, the first catalyst layer cumulatively effective at converting the gaseous alkane to its corresponding gaseous unsaturated carboxylic acid; wherein the catalysts of the first layer are impregnated on a metal oxide support; and (2) a second catalyst layer comprising one or more catalysts cumulatively effective at converting the gaseous unsaturated carboxylic acid to its corresponding gaseous ester;

wherein the second catalyst layer is separated at a distance downstream from the first catalyst layer and the reactor is operated at a temperature of from 500° C. to 1000° C., with a reactor residence time of no greater than 100 milliseconds; and wherein the one or more cracking catalysts is separated at a distance upstream relative to the flow of the gaseous stream of reactants to the short contact time reactor.

According to one embodiment, an additional catalyst layer is included between the first and second layers comprising at least one metal oxide including the metals Mo, Fe, P, V and combinations thereof, the catalyst additional layer cumulatively effective at converting the gaseous saturated carboxylic acid to its corresponding gaseous unsaturated carboxylic acid.

The invention also provides a multi-stage process for converting alkanes to their corresponding esters of unsaturated carboxylic acids, the process comprising the steps of:
  (a) passing 5-30% by weight of a gaseous alkane, and a stoichiometric amount of molecular oxygen, fully oxidizing the alkane to carbon dioxide and water vapor in the form of steam;
  (b) combining the steam and the remaining amount of alkane with the steam and carbon dioxide and directing it to contact one or more steam cracking catalysts;
  (c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof, and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid;
  (d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid; and
  (e) passing a second gaseous stream comprising an alcohol to the reactor;
  wherein the one or more cracking catalysts is separated at a distance upstream relative to the direction of flow of the gaseous stream to the first and second catalysts in first and second reaction zones comprising the short contact time reactor; the reactor containing one or more oxidation catalysts cumulatively effective for converting the alkene to an ester of its corresponding unsaturated carboxylic acid with the alcohol;
  the one or more oxidation catalysts comprising a first catalyst system effective for converting the alkane to its corresponding unsaturated carboxylic acid and a second catalyst effective for converting the ethylenically unsaturated alcohol, in the presence of the alcohol, to an ester of its corresponding ethylenically unsaturated carboxylic acid with the alcohol;
  the first catalyst being disposed in a first reaction zone;
  the second catalyst being disposed in a second reaction zone;
  the first reaction zone being disposed upstream of the second reaction zone relative to the direction of flow of the first gaseous stream through the reactor;
  the second gaseous stream being fed to the reactor intermediate the first reaction zone and the second reaction zone;
  the first reaction zone being operated at a temperature of from 500° C. to 1000° C., with a first reaction zone residence time of no greater than 100 milliseconds;
  the second reaction zone being operated at a temperature of from 300° C. to 400° C., with a second reaction zone residence time of no greater than 100 milliseconds.

The invention also provides a multi-stage process for the production of higher unsaturated carboxylic acids, the process comprising the steps of;
  (a) passing 5-30% by weight of a gaseous alkane, and a stoichiometric amount of molecular oxygen, fully oxidizing the alkane to carbon dioxide and water vapor in the form of steam;
  (b) combining the steam and the remaining amount of alkane with the steam and carbon dioxide and directing it to contact one or more steam cracking catalysts;
  (c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof; and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid;
  (d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid;
  (e) passing a first gaseous stream comprising an alkane and molecular oxygen to a reactor; and
  (f) passing a second gaseous stream comprising an aldehyde to the reactor;
  wherein the one or more cracking catalysts is separated at a distance upstream relative to the direction of flow of the gaseous stream to the first and second catalysts in first and second reaction zones comprising the short contact time reactor; the reactor containing one or more oxidation catalysts cumulatively effective for converting the alkane to its corresponding higher analogue of an unsaturated carboxylic acid;
  the one or more oxidation catalysts comprising a first catalyst system effective for converting the alkane to its corresponding saturated carboxylic acid and a second catalyst effective for converting the saturated carboxylic acid, in the presence of the aldehyde, to its corresponding higher analogue unsaturated carboxylic acid with the aldehyde;
  the first catalyst being disposed in a first reaction zone;
  the second catalyst being disposed in a second reaction zone;
  the first reaction zone being disposed upstream of the second reaction zone relative to the direction of flow of the first gaseous stream through the reactor;
  the second gaseous stream being fed to the reactor intermediate the first reaction zone and the second reaction zone;
  the first reaction zone being operated at a temperature of from 500° C. to 1000° C., with a first reaction zone residence time of no greater than 100 milliseconds;
  the second reaction zone being operated at a temperature of from 300° C. to 400° C., with a second reaction zone residence time of no greater than 100 milliseconds.

The invention also provides a multi-stage process for an alkane to its corresponding unsaturated carboxylic acids, the process comprising the steps of:
(a) passing 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more steam cracking catalysts;
(c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof; and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid; and
(d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid;
wherein the one or more cracking catalysts is separated at a distance upstream relative to the direction of flow of the gaseous stream to the first and second catalysts in first and second reaction zones comprising the short contact time reactor; the reactor containing one or more oxidation catalysts cumulatively effective for converting the alkene to its corresponding unsaturated carboxylic acid;
the one or more oxidation catalysts comprising at least one steam cracking catalyst effective for converting the alkane to its corresponding alkene, a first and second catalyst effective for the alkene to its corresponding saturated carboxylic acid and unsaturated carboxylic acid, and a third catalyst effective for converting the saturated carboxylic acid to its corresponding unsaturated carboxylic acid;
the first catalyst being disposed in a first reaction zone;
the second catalyst being disposed in a second reaction zone;
the third catalyst being disposed in a third reaction zone;
the first reaction zone being disposed upstream of the second reaction zone relative to the direction of flow of the first gaseous stream through the reactor;
the second reaction zone being disposed upstream of the third reaction zone relative to the direction of flow of the first gaseous stream through the reactor;
the second gaseous stream being fed to the reactor intermediate the second reaction zone and the third reaction zone;
the first reaction zone being operated at a temperature of from 500° C. to 1000° C., with first reaction zone residence time of no greater than 100 milliseconds;
the second reaction zone being operated at a temperature of from 300° C. to 400° C., with a second reaction zone residence time of no greater than 100 milliseconds;
the third reaction zone being operated at a temperature of from 100° C. to 300° C., with a third reaction zone residence time of no greater than 100 milliseconds.

The invention provides a multi-stage process for converting an alkane to a corresponding higher analogue unsaturated carboxylic acids, the process comprising the steps of:
(a) passing 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more steam cracking catalysts;
(c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof; and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid; and
(d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid; and
(e) passing a second gaseous stream comprising an aldehyde to the reactor;
wherein the one or more cracking catalysts is separated at a distance upstream relative to the direction of flow of the gaseous stream to the first and second catalysts in first and second reaction zones comprising the short contact time reactor;
the reactor containing one or more oxidation catalysts cumulatively effective for the oxidation of the alkane to its corresponding unsaturated carboxylic acid with the aldehyde;
the one or more oxidation catalysts comprising a first catalyst effective for converting the alkane to its corresponding alkene, a second catalyst effective for converting the alkene to its corresponding saturated carboxylic acid, and a third catalyst effective for converting the saturated carboxylic acid, in the presence of an aldehyde, to its corresponding higher analogue unsaturated carboxylic acid with the aldehyde;
the first catalyst being disposed in a first reaction zone;
the second catalyst being disposed in a second reaction zone;
the third catalyst being disposed in a third reaction zone;
the first reaction zone being disposed upstream of the second reaction zone relative to the direction of flow of the first gaseous stream through the reactor;
the second reaction zone being disposed upstream of the third reaction zone relative to the direction of flow of the first gaseous stream through the reactor;
the second gaseous stream being fed to the reactor intermediate the second reaction zone and the third reaction zone;

the first reaction zone being operated at a temperature of from 500° C. to 1000° C., with first reaction zone residence time of no greater than 100 milliseconds;

the second reaction zone being operated at a temperature of from 300° C. to 400° C., with a second reaction zone residence time of no greater than 100 milliseconds;

the third reaction zone being operated at a temperature of from 100° C. to 300° C., with a third reaction zone residence time of no greater than 100 milliseconds.

The invention provides a multi-stage process for converting an alkane to a corresponding higher analogue ester of an unsaturated carboxylic acids, the process comprising the steps of:

(a) passing 5-30% by weight of a gaseous alkane, and a stoichiometric amount of molecular oxygen, fully oxidizing the alkane to carbon dioxide and water vapor in the form of steam;

(b) combining the steam and the remaining amount of alkane with the steam and carbon dioxide and directing it to contact one or more steam cracking catalysts;

(c) catalytically converting the corresponding alkene generated from (b) and molecular oxygen to a short contact time reactor, the reactor including a mixed catalyst bed comprising at least one catalytic zone, a first catalytic zone further comprising: (1) at least one metal selected from the group consisting of Ag, Au, Ir, Ni, Pd, Pt, Rh, Ru, alloys thereof and combinations thereof; and (2) at least one modifier selected from the group of metal oxides including the metals Bi, In, Mg, P, Sb, Zr, Group 1-3 metals, lanthanide metals and combinations thereof, in combination with or without (3) at least one metal oxide including the metals Cd, Co, Cr, Cu, Fe, Mn, Ni, Nb, Ta, V, Zn, binary combinations thereof, ternary combinations thereof and higher combinations thereof, the catalyst converting the corresponding gaseous alkene to a gaseous stream including a corresponding gaseous unsaturated carboxylic acid and saturated carboxylic acid;

(d) passing the gaseous stream on to a second catalyst zone including a catalyst impregnated on a metal oxide support, the catalyst comprising at least one metal oxide including the metals Mo, Fe, P, V and combinations thereof, the catalyst zones cumulatively effective at converting the gaseous saturated carboxylic acids to its corresponding gaseous unsaturated carboxylic acid;

(e) passing a second gaseous stream comprising an aldehyde including formaldehyde to the reactor; and (f) passing a third gaseous stream comprising an alcohol to the reactor;

the reactor containing one or more oxidation catalysts cumulatively effective for converting the alkane to its corresponding higher analogue ester of an unsaturated carboxylic acid with the aldehyde and the alcohol;

the one or more oxidation catalysts comprising a first catalyst system effective for converting the alkane to its corresponding saturated carboxylic acid, a second catalyst effective for converting the saturated carboxylic acid, in the presence of the aldehyde, to its corresponding higher analogue unsaturated carboxylic acid, and a third catalyst effective for converting the higher analogue unsaturated carboxylic acid, in the presence of the alcohol, to an higher analogue ester of its corresponding unsaturated carboxylic acid with the alcohol;

the first catalyst system being disposed in a first reaction zone;

the second catalyst being disposed in a second reaction zone;

the third catalyst being disposed in a third reaction zone;

wherein the one or more cracking catalysts is separated at a distance upstream relative to the direction of flow of the gaseous stream to the first and second catalysts in first and second reaction zones comprising the short contact time reactor;

the first reaction zone being disposed upstream of the second reaction zone relative to the direction of flow of the first gaseous stream through the reactor;

the second reaction zone being disposed upstream of the third reaction zone relative to the direction of flow of the first gaseous stream through the reactor; the second gaseous stream being fed to the reactor intermediate the first reaction zone and the second reaction zone; the third gaseous stream being fed to the reactor intermediate the second reaction zone and the third reaction zone;

the first reaction zone being operated at a temperature of from 500° C. to 1000° C., with first reaction zone residence time of no greater than 100 milliseconds;

the second reaction zone being operated at a temperature of from 300° C. to 400° C., with a second reaction zone residence time of no greater than 100 milliseconds;

the third reaction zone being operated at a temperature of from 100° C. to 300° C., with a third reaction zone residence time of no greater than 100 milliseconds.

The invention also provides a multi-stage recycle process comprising the steps of: (a) converting an alkane to its corresponding products selected from alkene using one or more steam cracking catalysts, (b) converting the corresponding alkene to further oxygenated products selected from unsaturated carboxylic acid, and higher analogue unsaturated carboxylic acid in a short contact time reactor using the catalyst systems of the invention; and (c) adding the resulting product or products to the front end of a second fixed bed oxidation reactor under short contact time conditions with the product(s) from the first steam cracking reactor acting as feed to the second reactor. According to one embodiment this includes feeding any unreacted alkane from the first steam cracking reactor and any unreacted alkene from the short contact time reactor to the short contact time reactor reactor to recycle the respective alkane and alkene.

The invention also provides a multi-stage process for converting an alkane to its corresponding products selected from unsaturated carboxylic acid, higher analogue unsaturated carboxylic acid and ester thereof comprising the step of providing a thermal gradient having the cumulative effect of improving conversion of the alkane to a desired oxygenated product.

The invention also provides a multi-stage process for converting an alkane to its corresponding products selected from unsaturated carboxylic acid, higher analogue unsaturated carboxylic acid and ester thereof comprising the step of providing a catalytic cascade further comprising one or more catalytic systems having the cumulative effect of improving conversion of the alkane to a desired oxygenated product.

As used herein the term "multi-stage process" refers to a combination of two or more stages including two or more reactors, each reactor comprising at least one catalyst, the reactors further comprising a combination of at least one catalytic reactor with at least one catalyst in a short contact time reactor which effects the cumulative conversion of one or more alkanes to one or more corresponding oxygenated products. According to one embodiment the multi-stage process comprises a steam cracking reactor in combination with at least one catalyst in a short contact time reactor, the steam cracking reactor converting one or more alkanes to one or more corresponding alkenes and the shorts contact time reactor converting the corresponding one or more alkenes to one or more further corresponding oxygenated products.

As used herein, the term "cumulatively converting" refers to producing a desired product stream from one or more specific reactants using catalyst systems of the invention under specific reaction conditions. As an illustrative example, cumulatively converting an alkane to an ester of its corresponding unsaturated carboxylic acid with an alcohol means that the catalyst(s) utilized will produce a product stream comprising an ester of the added alcohol with the unsaturated carboxylic acid corresponding to the added alkane when acting on a feed stream(s) comprising the alkane and the alcohol under the designated reaction conditions.

As used herein the term "catalytic system" refers to two or more catalysts. The term "multi-stage catalytic system" refers to one or more steam cracking catalysts in combination with one or more oxidation catalysts for cumulatively converting alkenes to corresponding oxygenated products. For example, platinum metal and indium oxide impregnated on an alumina support defines a catalytic system. Another example is niobium oxide impregnated on platinum gauze. Yet another example is palladium metal, vanadium oxide and magnesium oxide impregnated on silica.

Accordingly, the present invention relates to multi-staged oxidation/dehydrogenation catalysts and multi-stage processes for preparing dehydrogenated products and oxygenated products from alkanes and oxygen at short contact times. Suitable alkanes include alkanes having straight or branched chains. Examples of suitable alkanes include $C_3$-$C_{25}$ alkanes, preferably $C_3$-$C_8$ alkanes such as propane, butane, isobutane, pentane, isopentane, hexane and heptane. Particularly preferred alkanes are propane and isobutane.

Multi-staged catalyst systems of the invention cumulatively convert alkanes to their corresponding alkenes and oxygenates including saturated carboxylic acids, unsaturated carboxylic acids, esters thereof, and higher analogue unsaturated carboxylic acids and esters thereof. The catalytic systems are designed to provide a specific alkene, oxygenate and combinations thereof. According to one embodiment, use of one or more conventional steam cracking catalysts, alkanes are catalytically converted to corresponding alkenes. The corresponding alkenes produced in the cracking reactor are directed to one or more oxidation catalysts in a short contact reactor to provide corresponding oxygenated products. According to a separate embodiment, any unreacted alkane, alkene or intermediate is recycled to catalytically convert it to its corresponding oxygenate in accordance with the invention. According to a separate embodiment, alkenes produced from dehydrogenation of corresponding alkanes using steam cracking catalysts or catalytic systems of the invention are deliberately produced as in-process chemical intermediates and not isolated as corresponding alkenes before selective partial oxidation to further corresponding oxygenated products. For example, when catalytically converting an alkane to its corresponding ethylenically unsaturated carboxylic acid, any unreacted alkene produced is recovered or recycled to catalytically convert it to its corresponding ethylenically unsaturated carboxylic acid product stream.

According to one embodiment, the alkane is also catalytically converted to its corresponding alkene intermediates through two or more steam cracking catalytic zones. For example, propane is converted to propylene through a steam cracking reactor. According to a separate embodiment, an alkane is catalytically converted to its corresponding saturated carboxylic acid in a first and second stage catalytic zone or layer of a mixed hybrid catalyst bed. The saturated carboxylic acid, in the presence of an additional formaldehyde stream, to its corresponding higher analogue ethylenically unsaturated carboxylic acid in a second catalytic zone or layer of a mixed bed catalyst. In a specific example, propane is catalytically converted to propionic acid and the propionic acid in the presence of formaldehyde is catalytically converted to methacrylic acid.

As used herein, the term "higher analogue unsaturated carboxylic acid" and "ester of a higher analogue unsaturated carboxylic acid" refer to products having at least one additional carbon atom in the final product as compared to the alkane or alkene reactants. For example given above, propane ($C_3$ alkane) is converted to propionic acid ($C_3$ saturated carboxylic acid), which in the presence of formaldehyde is converted to its corresponding higher analogue ($C_4$) carboxylic acid, methacrylic acid using catalysts of the invention.

Suitable alkenes used in the invention include alkenes having straight or branched chains. Examples of suitable alkenes include $C_3$-$C_{25}$ alkenes, preferably $C_3$-$C_8$ alkenes such as propene (propylene), 1-butene (butylene), 2-methylpropene (isobutylene), 1-pentene and 1-hexene. Particularly preferred alkenes are propylene and isobutylene.

Suitable aldehydes used in the invention include for example formaldehyde, ethanal, propanal and butanal.

Steam cracking catalyst systems of the invention convert alkanes to their corresponding alkenes. Oxidation catalyst systems convert corresponding alkenes to further corresponding oxygenates including unsaturated and saturated carboxylic acids having straight or branched chains. Multi-staged catalyst systems cumulatively convert corresponding alkanes to corresponding alkenes and further corresponding oxygenates including but not limited to unsaturated and saturated carboxylic acids having straight or branched chains. Examples include $C_3$-$C_8$ saturated carboxylic acids such as propionic acid, butanoic acid, isobutyric acid, pentanoic acid and hexanoic acid. According to one embodiment, saturated carboxylic acids produced from corresponding alkanes using catalyst systems of the invention are deliberately produced as in-process chemical intermediates and not isolated before selective partial oxidation to oxygenated products including unsaturated carboxylic acids, esters of unsaturated carboxylic acids, and higher esters of unsaturated carboxylic acids. According to a separate embodiment, any saturated carboxylic acid produced is converted using catalysts of the invention to its corresponding product stream including an ethylenically unsaturated carboxylic acid, esters thereof, a higher analogue unsaturated carboxylic acid or esters thereof.

According to one embodiment, certain oxidation catalyst systems cumulatively covert alkenes to their corresponding oxygenated products and multi-staged catalyst systems of the invention cumulatively convert alkanes to their corresponding ethylenically unsaturated carboxylic acids and higher analogues having straight or branched chains. Examples include $C_3$-$C_8$ ethylenically unsaturated carboxylic acids such as acrylic acid, methacrylic acid, butenoic acid, pentenoic acid, hexenoic acid, maleic acid, and crotonic acid. Higher analogue ethylenically unsaturated carboxylic acids are prepared from corresponding alkanes and aldehydes. For example, methacrylic acid is prepared from propane and formaldehyde. According to a separate embodiment, the corresponding acid anhydrides are also produced when preparing ethylenically unsaturated carboxylic acids from their respective alkanes. The catalysts of the invention are usefully employed to convert propane to acrylic acid and its higher unsaturated carboxylic acid methacrylic acid and to convert isobutane to methacrylic acid.

According to one embodiment, certain oxidation catalyst systems of the invention are also advantageously utilized converting alkenes to their corresponding esters of unsaturated carboxylic acids and higher analogues and multi-staged catalyst systems of the invention are also advantageously utilized for cumulatively converting alkenes to their corresponding esters of unsaturated carboxylic acids and higher analogues. Specifically, these esters include, but are not limited to, butyl acrylate from butyl alcohol and propane, β-hydroxyethyl acrylate from ethylene glycol and propane, methyl methacrylate from methanol and isobutane, butyl methacrylate from butyl alcohol and isobutane, β-hydroxyethyl methacrylate from ethylene glycol and isobutane, and methyl methacrylate from propane, formaldehyde and methanol.

In addition to these esters, other esters are formed through this invention by varying the type of alcohol introduced into the reactor and/or the alkane, alkene and corresponding oxygenates introduced into the reactor.

Suitable alcohols include monohydric alcohols, dihydric alcohols and polyhydric alcohols. Of the monohydric alcohols reference may be made, without limitation, to $C_1$-$C_{20}$ alcohols, preferably $C_1$-$C_6$ alcohols, most preferably $C_1$-$C_4$ alcohols. The monohydric alcohols may be aromatic, aliphatic or alicyclic; straight or branched chain; saturated or unsaturated; and primary, secondary or tertiary. Particularly preferred monohydric alcohols include methyl alcohol, ethyl alcohol, propyl alcohol, isopropyl alcohol, butyl alcohol, isobutyl alcohol and tertiary butyl alcohol. Of the dihydric alcohols reference may be made, without limitation, to $C_2$-$C_6$ diols, preferably $C_2$-$C_4$ diols. The dihydric alcohols may be aliphatic or alicyclic; straight or branched chain; and primary, secondary or tertiary. Particularly preferred dihydric alcohols include ethylene glycol (1,2-ethanediol), propylene glycol (1,2-propanediol), trimethylene glycol (1,3-propanediol), 1,2-butanediol and 2,3-butanediol. Of the polyhydric alcohols reference will only be made to glycerol (1,2,3-propanetriol).

The unsaturated carboxylic acid corresponding to the added alkane is the α,β-unsaturated carboxylic acid having the same number of carbon atoms as the starting alkane and the same carbon chain structure as the starting alkane, e.g., acrylic acid is the unsaturated carboxylic acid corresponding to propane and methacrylic acid is the unsaturated carboxylic acid corresponding to isobutane.

Similarly, the unsaturated carboxylic acid corresponding to an alkene is the α,β-unsaturated carboxylic acid having the same number of carbon atoms as the alkene and the same carbon chain structure as the alkene, e.g., acrylic acid is the unsaturated carboxylic acid corresponding to propene and methacrylic acid is the unsaturated carboxylic acid corresponding to isobutene.

Likewise, the unsaturated carboxylic acid corresponding to an unsaturated aldehyde is the α,β-unsaturated carboxylic acid having the same number of carbon atoms as the unsaturated aldehyde and the same carbon chain structure as the unsaturated aldehyde, e.g., acrylic acid is the unsaturated carboxylic acid corresponding to acrolein and methacrylic acid is the unsaturated carboxylic acid corresponding to methacrolein.

The alkene corresponding to the added alkane is the alkene having the same number of carbon atoms as the starting alkane and the same carbon chain structure as the starting alkane, e.g., propene is the alkene corresponding to propane and isobutene is the alkene corresponding to isobutane. (For alkenes having four or more carbon atoms, the double bond is in the 2-position of the carbon-carbon chain of the alkene.)

The unsaturated aldehyde corresponding to the added alkane is the a,13-unsaturated aldehyde having the same number of carbon atoms as the starting alkane and the same carbon chain structure as the starting alkane, e.g., acrolein is the unsaturated aldehyde corresponding to propane and methacrolein is the unsaturated carboxylic acid corresponding to isobutane.

Similarly, the unsaturated aldehyde corresponding to an alkene is the α,β-unsaturated carboxylic acid having the same number of carbon atoms as the alkene and the same carbon chain structure as the alkene, e.g., acrolein is the unsaturated aldehyde corresponding to propene and methacrolein is the unsaturated aldehyde corresponding to isobutene.

With respect to the metals used in the catalysts of the inventions, the following definitions based on the Periodic Table apply:

Group 1 comprises Li, Na, K, Rb and Cs.
Group 2 comprises Mg, Ca, Sr and Ba.
Group 3 comprises B, Al, Ga, In and Tl.
Lanthanides comprises Sc, Y, La, Ce, Pr, Nd, Pm, Sm, Eu, Gd, Tb, Dy, Ho, Er, Tm, Yb, Lu and all stable elements of the actinide series.
Group 4A comprises C, Si, Ge, Sn and Pb.
Group 4B comprises Ti, Zr and Hf.
Group 5A comprises N, P, As, Sb and Bi.
Group 5B comprises V, Nb and Ta.
Group 6B comprises Cr, Mo and W.
Group 7B comprises Mn, Tc and Re.
Group 8 comprises Fe, Ru, Os, Co, Rh, Ir, Ni, Pd and Pt.

Accordingly, the present invention provides a supported catalyst system for converting alkanes to their corresponding alkenes under steam cracking conditions and for converting alkenes to corresponding oxygenates at short contact times.

The support structure is three-dimensional, i.e. the support has dimensions along an x, y and z orthogonal axes of a Cartesian coordinate system, and affords a relatively high surface area per unit volume. Though lower and higher amounts are possible, in one embodiment, the support structure exhibits a surface area of 0.01 to 50 $m^2$/g, preferably 0.1 to 10 $m^2$/g.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above noted general criteria. Examples of suitable physical forms include foam, honeycomb, lattice, mesh, monolith, woven fiber, nonwoven fiber, gauze, perforated substrates (e.g., foil), particle compacts, fibrous mat and mixtures thereof. For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses, as well as others.

The support structure may be fabricated from a material that is inert to the reaction environment of the catalytic reaction. Suitable materials include ceramics and their isomorphs such as silica, alumina (including α-, β- and γ-isomorphs), silica-alumina, aluminosilicate, zirconia, titania, boria, mullite, lithium aluminum silicate, oxide-bonded silicon carbide, metal alloy monoliths, Fricker type metal alloys, FeCrAl alloys and mixtures thereof. (Alternatively, the catalyst may be prepared so as to define the support structure itself, e.g., by "green" compacting or another suitable technique.)

The catalysts may be applied to the support structure using any suitable art-disclosed technique. For instance, the catalyst may be vapor deposited (e.g., by sputtering, plasma deposition or some other form of vapor deposition). The catalyst may be impregnated or coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

The multi-staged catalyst system of the invention cumulatively converts alkanes to their corresponding alkenes and oxygenates. The steam cracking catalyst comprises at least one steam cracking catalysts. The oxidation catalyst under short contact times comprises three components: (a) at least one metal selected from the group consisting of Ag, Au, Ir, Ni, Pd, Pt, Rh, Ru, alloys thereof and combinations thereof; and (b) at least one modifier selected from the group of metal oxides including the metals Bi, In, Mg, P, Sb, Zr, Group 1-3 metals, lanthanide metals and combinations thereof, in combination with or without (c) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts are impregnated on a metal oxide support.

Catalytic component (a) is a promoter usefully employed to oxidatively dehydrogenate alkanes to their corresponding alkenes. The catalyst is present on the support in the form of finely dispersed metal particles including alloys (microns to nanometers) having high surface area. Alternatively, the catalyst is in the form of a fine gauze, including nanometer sized wires. The catalyst is impregnated on the support using techniques selected from metal sputtering, chemical vapor deposition, chemical and/or electrochemical reduction of the metal oxide. Combinations of promoters and their alloys are useful employed. The catalytic system component comprises metal oxides and metal oxides used in combination with promoters.

Catalytic component (b) is a modifier usefully employed to partially oxidize alkanes to their corresponding saturated carboxylic acids and unsaturated carboxylic acids. Metal oxides catalysts are in the form of binary, ternary, quaternary or higher order mixed metal oxides. The reducible metal oxide may be an oxide of a metal selected from the group consisting of Bi, In, Mg, P, Sb, Zr, Group 1-3 metals, Y, Sc, La, Zr, Ta, Ce, Pr, Nd, Pm, Sm, Eu, Gd, Tb, Dy, Ho, Er, Tm, Yb, Lu and mixtures thereof. The modifier may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

Catalytic component (c) is usefully employed to partially oxidize alkanes to their corresponding alkenes, saturated carboxylic acids and unsaturated carboxylic acids. Metal oxides catalysts are in the form of binary, ternary, quaternary or higher order mixed metal oxides. The reducible metal oxide may be an oxide of a metal selected from the group consisting of Cu, Cd, Co, Cr Fe, V, Mn, Ni, Nb, Mo, W, Re, Ga, Ge, In, Sn, Sb, Tl, Pb, Bi, Te, As, Se, V, Zn, Y, Zr, Ta and mixtures thereof. Preferably, the reducible metal oxide is selected from the group consisting of metals Cd, Co, Cr, Cu, Fe, Mn, Ta, V and combinations thereof and mixtures thereof. The promoter is a metal selected from Fe, Ru, Os, Co, Rh, Ir, Ni, Pd and Pt, preferably a metal selected from the group consisting of Pt, Pd, Rh, Ir, Ru and mixtures thereof. The promoter may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition. The catalyst is present on the support in the form of finely dispersed metal oxide particles (microns to nanometers) having high surface area. The catalytic system component comprises metal oxides and metal oxides used in combination with promoters in contact with a metal oxide supported.

According to one embodiment the catalyst system comprises catalysts (a) and (b). According to a separate embodiment, catalyst system comprises a combination of catalyst (a), (b) and (c). The catalyst are typically in contact with (preferably impregnated on) a metal oxide support having a three-dimensional structure.

The various mixed metal oxides of the present invention, as noted above, may be prepared in the following manner.

In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain the elements required for the particular catalyst, as previously defined.

Suitable solvents include water, alcohols including, but not limited to, methanol, ethanol, propanol, and diols, etc., as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed at the time of mixing.

For example, when a mixed metal oxide of the formula $Mo_aV_bTe_cNb_dO_e$ is to be prepared, an aqueous solution of telluric acid, an aqueous solution of niobium oxalate and a solution or slurry of ammonium paramolybdate may be sequentially added to an aqueous solution containing a predetermined amount of ammonium metavanadate, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally employed.

Once obtained, the catalyst precursor is calcined. The calcination is usually conducted in an oxidizing atmosphere, but it is also possible to conduct the calcination in a non-oxidizing atmosphere, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 1000° C., including from 400° C. to 900° C., and including from 500° C. to 800° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In one mode of operation, the catalyst precursor is calcined in two stages. In the first stage, the catalyst precursor is calcined in an oxidizing atmosphere (e.g., air) at a temperature of from 200° C. to 400° C., including from 275° C. to 325° C. for from 15 minutes to 8 hours, including from 1 to 3 hours. In the second stage, the material from the first stage is calcined in a non-oxidizing environment (e.g., an inert atmosphere) at a temperature of from 500° C. to 900° C., including from 550° C. to 800° C., for from 15 minutes to 8 hours, including from 1 to 3 hours.

Optionally, a reducing gas, such as, for example, ammonia or hydrogen, is added during the second stage calcination.

In a separate mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gases) through the bed of solid catalyst precursor particles.

With calcination, a mixed metal oxide catalyst is formed having a stoichiometric or non-stoichiometric amounts of the respective elements.

The invention provides also process for preparing metal oxide and mixed metal oxide catalysts that convert alkanes to their corresponding alkenes and oxygenates at short contact times comprising the steps of;

mixing salts of metals selected from the group consisting of Mo, Te, V, Ta and Nb at temperatures above the melting point of the highest melting salt to form a miscible molten salt; and calcining the mixture of salts in the presence of oxygen to provide a mixed metal oxide catalyst, optionally using a metal halide salt or a metal oxyhalide salt as solvent.

The starting materials for the above mixed metal oxide are not limited to those described above. A wide range of materials including, for example, oxides, nitrates, halides or oxyhalides, alkoxides, acetylacetonates and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

Use of low-melting salts opens up a new approach to preparing mixed metal oxide catalysts. The advantages over current aqueous suspension methods include higher incorporation of sparsely soluble metal salts, better control of metal ratios, and more homogeneous catalyst systems. One unique approach is to use low-melting halides of the desired MMO metals to prepare salt solutions. Variations of this approach are discussed below in more detail.

Halide salts of the desired metals are combined by mixing at temperatures above the melting point of the highest melting salt. The molten salts should be miscible with each other forming a stable, homogeneous solution of molten salt.

One advantage of the method is that it eliminates the solubility limits inherent in aqueous slurry systems. By using molten salts, we can incorporate much higher levels of such metals as niobium, vanadium, and palladium, the salts of which have relatively low solubilities in aqueous media. Examples of metal salts and their melting points are given in Table 4. These salts are readily available, relatively inexpensive, and have reasonably low melting points.

According to one embodiment, certain metal oxyhalides are useful as solvents in preparing metal oxides using the method. Vanadium halides such as vanadium tetrachloride, $VCl_4$ and vanadyl trichloride ($VOCl_3$), which are liquids at room temperature and are ideal solvents for the chloride salts of the other metals because of their polarity and low boiling points (BP($VCl_4$)=148° C., BP($VOCl_3$)=127° C.). Metal halides are dissolved in one of these solvents in the desired mole ratios, and then excess vanadium is removed via evaporation under reduced pressure and inert atmosphere. The catalyst cake is then calcined under $O_2$/Argon to liberate oxides of chlorine, generating the mixed metal oxide catalyst. Alternatively, the catalyst cake can be calcined under wet Argon to generate the mixed metal oxide (MMO) catalyst and HCl. In addition, mixed metal halides (MMH) are also converted to MMO, discussed in more detail below.

According to a separate embodiment, it is advantageous to introduce oxygen earlier in the synthesis. This is achieved by mixing metal oxides into either the molten salt solution or the $VCl_4/VOCl_3$ solution. This method reduces the amount of chlorine that must be removed during calcination and generates mixed oxychloride precursors that already have some of the desired characteristics of the final catalyst. One preparation is to dissolve oxides of niobium, tellurium, and molybdenum in $VCl_4/VOCl_3$. The resulting precursor will already have high oxygen content.

According to a separate embodiment, mixed metal halides (MMH) are also converted to MMO. Three methods for converting mixed metal halides (MMH) and mixed metal oxyhalides (MMOH) to mixed metal oxides (MMO) are described:

(A) MMH precursors are calcined under wet (1%) argon at elevated temperatures (600° C.). The off-gas is scrubbed with caustic to trap the product HCl.

(B) MMH precursors are calcined under argon with low $O_2$ concentration. The low $O_2$ concentration moderates the reaction. The oxychloride gases is scrubbed with caustic.

(C) MMH precursors are chemically converted to the metal alkoxides under mild conditions, followed by calcination under $O_2$/Argon to generate the MMO catalyst. By using the alkoxide intermediate, the crystalline structure of the final catalyst can be altered.

The MMO prepared from the molten salt method can be prepared on support materials including metal oxide supports. One advantage of using molten salt or salt solutions in $VCl_4/VOCl_3$ is that it is comparatively easy to impregnate support material, such as alumina, zirconia, silica, or titanium oxide, and allows the use of either the pearl technique or sequential loading. The relatively high metal concentrations in solution enables one to increase the metal loading on the support material, providing an ideal catalyst for millisecond contact time reactions.

Alternatively, another approach to preparing supported MMO catalyst is addition of finely-divided support material such as aluminum oxide into the salt solution (molten salt or $VCl_4/VOCl_3$ solution) to create a suspension/slurry. After concentration and calcination, the final catalyst prepared is a supported MMO catalyst with significantly higher surface area.

A mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide; the viscosity, the concentration, etc. of the solvent used in the case of wet grinding; or the optimum conditions of the grinding apparatus. However, it is preferred that grinding is conducted until the average particle size of the ground catalyst precursor would usually be at most 20 µm, more preferably at most 5 µm. Improvement in the catalytic performance may be brought about by such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying. Further, similar drying may be conducted also in the case where wet grinding is conducted.

The oxide obtained by the above-mentioned method may be used as a final catalyst, but it may further be subjected to heat treatment usually at a temperature of from 200° to 800° C. for from 0.1 to 10 hours.

The mixed metal oxide thus obtained is typically used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution support), and the solution agitated such that the metal ions are ion-exchanged onto the support. The metal containing support is then dried and calcined as detailed above.

When using a catalyst system including two or more catalysts, the catalyst may be in the form of a physical blend of the several catalysts. Preferably, the concentration of the catalysts may be varied so that the first catalyst component will have a tendency to be concentrated at the reactor inlet while subsequent catalysts will have a tendency to be concentrated in sequential zones extending to the reactor outlet. Most preferably, the catalysts will form a layered bed (also referred to a mixed bed catalyst), with the first catalyst component forming the layer closest to the reactor inlet and the subsequent catalysts forming sequential layers to the reactor outlet. The layers abut one another or may be separated from one another by a layer of inert material or a void space.

The short contact time reactor is of a type suitable for the use of a fixed catalyst bed in contact with a gaseous stream of reactants. For instance, a shell and tube type of reactor may be utilized, wherein one or more tubes are packed with catalyst(s) so as to allow a reactant gas stream to be passed in one end of the tube(s) and a product stream to be withdrawn from the other end of the tube(s). The tube(s) being disposed in a shell so that a heat transfer medium may be circulated about the tube(s).

In the case of the utilization of a single catalyst, hybrid catalyst, catalyst system or hybrid catalyst system, the gas stream comprising the alkane, molecular oxygen and any additional reactant feeds including but not limited to alkenes, oxygen, air, hydrogen, carbon monoxide, carbon dioxide, formaldehyde and alcohols, steam and any diluents including nitrogen, argon may all be fed into the front end(s) of the tube(s) together. Alternatively, the alkane and the molecular oxygen-containing gas may be fed into the front end(s) of the tube(s) while the additional reactants, steam and diluents may be fed (also referred to as staging) into the tube(s) at a predetermined downstream location (typically chosen so as to have a certain minimum concentration of product alkene present in the gas stream passing through the tube(s), e.g., 3%, preferably 5%, most preferably 7%).

In the case of the utilization of catalyst systems including two or more catalysts, e.g., a first catalyst component and a second catalyst component as described above, once again the gas stream comprising the alkane, the oxygen-containing gas and any additional reactant feeds including but not limited to alkenes, oxygen, air, hydrogen, carbon monoxide, carbon dioxide, formaldehyde and alcohols, steam and any diluents including nitrogen, argon are fed to the front end(s) of the tube(s) together. Alternatively, and preferably, the alkane and the molecular oxygen-containing gas are staged into the front end(s) of the tube(s) while any additional reactant feeds, steam and diluents are staged into the tube(s) at a predetermined downstream location (typically chosen so at have a certain minimum concentration of desired product present in the gas stream passing through the tube(s),as set forth above; or in the case of the utilization of layered beds of catalyst, as described above, intermediate two layered catalyst beds).

In addition to molecular oxygen, carbon dioxide is also employed as a much milder oxidizing agent in the multi-stage method of the invention. One advantage of the invention is that carbon dioxide is generated by sacrificing a small portion of the alkane in the initial step of steam cracking in addition to steam using conventional steam cracking catalysts well known in the art. In addition to providing a milder oxidant the exothermic nature of converting alkane to alkene is minimized which in turn minimizes over oxidation products, including but not limited to CO, alkane fragments and alkene fragments and combinations thereof. A second advantage is that unlike molecular oxygen, carbon dioxide will not induce gas-phase radical reactions. Such oxidative coupling reactions will be controlled by heterogeneous catalysts. As a consequence and according to an exemplary embodiment, methane can be oxidatively coupled to provide ethylene without over oxidation as well methane and ethane cane be combined and catalytically converted to propylene. Suitable catalysts include but are not limited to PbO/MgO, lanthanide oxides, mixtures of lanthanide oxides, $CaO/CeO_2$, metal oxides, combinations of Group 1-3 oxides and metal oxides such as $CaO/MnO_2$, $CaO/Cr_2O_3$, CaO/ZnO, combinations of metal oxides, multi-component metal oxide catalysts, supported metal oxides as described earlier such as $SiO_2/Cr_2O_3$, certain non metal oxides, certain non-oxide metals and combinations thereof.

According to a separate embodiment, alkanes, including but not limited to for example ethane, propane, isobutane, and butane are oxidized to their corresponding alkenes using carbon dioxide and steam in a steam cracking process by partially sacrificing some initial alkane to generate carbon dioxide as an oxidizing agent and combining the oxidant with the remaining corresponding alkane. Another advantage of the invention as described earlier is that unwanted reactions that lead to coking at higher temperatures are minimized in addition to complete oxidation of molecular hydrogen, allowing the oxidation to occur at lower temperatures, further minimizing over oxidation of the alkane. Suitable catalysts in addition to those described above include but are not limited to for example metal oxide catalysts, mixed metal oxide catalysts, multi-component metal oxide catalysts, including supported metal oxides as described earlier such as K—Cr—Mn/$SiO_2$, $SiO_2/Cr_2O_3$ and Fe/Mn silicate, and combinations thereof. Another advantage of carbon dioxide as an oxidant is that their redox properties dominates the catalytic process including unwanted radical processes. Carbon dioxide produces active oxygen species that act as oxidants, carbon dioxide reoxidizes reduced oxides forming a continuous redox cycle and carbon dioxide oxidizes carbon, reducing coking. Typical reaction conditions for the oxidation of alkanes to corresponding alkenes which are utilized in the practice of the present invention include: steam cracking reaction temperatures which can vary from 200° C. to 700° C. Conventional steam cracking reactors and catalysts are well known in the art and are described in the journal Energy & Fuels, 18 1126-1139, 2004.

Typical reaction conditions for the oxidation of alkenes including but not limited to for example ethylene, propylene, butylene or isobutylene to acrylic acid or methacrylic acid including respective esters thereof which are utilized in the practice of the present invention include: reaction temperatures which can vary from 300° C. to 1000° C., but are usually in the range of flame temperatures (from 500° C. to 1000° C.); the average contact time with the catalyst (i.e. the reactor residence time) is not more than 100 milliseconds, including not more than 80 milliseconds, and including not more than 50 milliseconds; the pressure in the reaction zone usually ranges from 0 to 75 psig, including no more than 50 psig.

The invention provides a multi-stage process for preparing unsaturated carboxylic acids from corresponding alkanes, the process comprising the steps of:
  (a) combining 5-30% by weight of a gaseous alkane, and a stoichiometric amount of molecular oxygen, fully oxidizing the alkane to carbon dioxide and water vapor in the form of steam;
  (b) combining the steam and the remaining amount of alkane with the steam and carbon dioxide and directing it to contact one or more stem cracking catalysts; and
  (c) converting the corresponding alkene generated from (b) and molecular oxygen to a short contact time reactor, the reactor including a mixed catalyst bed comprising (1) a first catalyst layer comprising (i) at least one metal selected from the group consisting of Ag, Au, Ir, Ni, Pd, Pt, Rh, Ru, alloys thereof and combinations thereof; and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts of the first layer are impregnated on a metal oxide support; and (2) a second catalyst layer comprising at least one metal oxide including the metals Mo, Fe, P, V and combinations thereof, the mixed bed catalyst cumulatively effective at converting the gaseous alkane to its corresponding gaseous unsaturated carboxylic acid;
  wherein the second catalyst layer is separated at a distance downstream from the first catalyst layer and the reactor is operated at a temperature of from 500° C. to 1000° C., with a reactor residence time of no greater than 100 milliseconds; and wherein the one or more cracking catalysts is separated at a distance upstream from the short contact time reactor.

As a separate embodiment, the present invention provides a multi-stage process for preparing unsaturated carboxylic acids from corresponding alkanes, the process comprising the steps of
  (a) combining 5-30% by weight of a gaseous alkane, and a stoichiometric amount of molecular oxygen, fully oxidizing the alkane to carbon dioxide and water vapor in the form of steam;

(b) combining the steam and the remaining amount of alkane with the steam and carbon dioxide and directing it to contact one or more stem cracking catalysts; and (c) converting the corresponding alkene generated from (b) and molecular oxygen to a short contact time reactor, the reactor including a mixed catalyst bed comprising (1) a first catalyst layer comprising (i) at least one metal selected from the group consisting of Ag, Au, Ir, Ni, Pd, Pt, Rh, Ru, alloys thereof and combinations thereof, and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts of the first layer are impregnated on a metal oxide support; and (2) a second catalyst layer comprising at least one metal oxide including the metals Mo, Fe, P, V and combinations thereof, the mixed bed catalyst cumulatively effective at converting the gaseous alkane to its corresponding gaseous unsaturated carboxylic acid;

wherein the one or more cracking catalysts is separated at a distance upstream from the short contact time reactor;

the first catalyst zone being disposed upstream of the second catalyst zone relative to the direction of flow of the gaseous stream through the reactor;

the first catalyst zone being operated at a temperature of from 500° C. to 1000° C., with a first reaction zone residence time of no greater than 100 milliseconds;

the second catalyst zone being operated at a temperature of from 300° C. to 400° C., with a second reaction zone residence time of no greater than 100 milliseconds;

wherein the gaseous stream of the alkane is passed through the reactor in a single pass or wherein any unreacted alkane is recycled back into the gaseous stream of alkane entering the reactor and wherein any saturated carboxylic acid is recycled back into the second catalyst zone to increase the overall yield of unsaturated carboxylic acid.

It is useful to pass a gaseous stream comprising propane or isobutane and molecular oxygen to the reactor. In addition, the feed may contain an additional reactant, adjuvant such as steam or a diluent such as an inert gas, e.g., nitrogen, argon or a milder oxidant including carbon dioxide.

In a separate embodiment, the gaseous stream of the alkane or alkene is passed through its respective SCR or SCTR in a single pass or wherein any unreacted alkane or alkene is recycled back into the gaseous stream of alkene entering its respective SCTR and any saturated carboxylic acid is recycled back into the second catalyst zone to increase the overall yield of unsaturated carboxylic acid.

The invention also provides a multi-stage process comprising the steps of: (a) cumulatively converting an alkane to its corresponding alkene using one or more steam cracking catalysts, (b) catalytically converting the corresponding alkene to further corresponding oxygenated products selected from unsaturated carboxylic acid, and higher analogue unsaturated carboxylic acid in a short contact time reactor using the catalyst systems of the invention; and (c) adding the resulting product or products to the front end of a second fixed bed oxidation reactor with the product(s) from the first reactor acting as feed to the second reactor. For example, propane is first steam cracked and catalytically converted to propylene and the propylene is further catalytically converted to corresponding oxygenates using a catalyst system in a short contact time reactor. The propylene is fed to the second oxidation reactor that converts its to acrylic acid. According to one embodiment this includes feeding any unreacted alkane from the first reactor and any unreacted alkene from the second reactor to recycle the respective alkane and alkene. For example, any unreacted propane is recycled to the first steam cracking reactor or SCR or optionally added as a feed to the second oxidation reactor. The second oxidation reactor comprises any conventional industrial scale oxidation reactor used for converting alkenes to unsaturated carboxylic acids at longer residence times (seconds). Alternatively, the second oxidation reactor comprises a second SCTR operating at millisecond residence times.

Any source of molecular oxygen may be employed in this process, e.g., oxygen, oxygen-enriched gases or air. Air may be the most economical source of oxygen, especially in the absence of any recycle.

Alternatively, the metal oxide catalyst components or second catalyst layer may comprise:

(A) a mixed metal oxide catalyst having the empirical formula $$Mo_aV_bM_cN_dO_e$$

wherein

M is selected from the group consisting of Te and Sb,

N is at least one element selected from the group consisting of Nb, Ta, W, Ti, Al, Zr, Cr, Mn, B, In, As, Ge, Sn, Li, Na, K, Rb, Cs, Fr, Be, Mg, Ca, Sr, Ba, Hf and P, a, b, c, d and e represent relative atomic amounts of the elements, and when a=1, b=0.01 to 1.0, c=0.01 to 1.0, d=0.01 to 1.0 and e depends on the oxidation state of the elements other than oxygen. At flame temperatures, certain metal components, including Mo and Te, of the mixed metal oxide catalyst volatilize leaving different mixed metal oxide catalysts, intermetallic catalysts and hybrid catalysts thereof.

(B) a catalyst comprising a mixed metal oxide having the empirical formula $$Mo_aSb_bO_c$$

wherein a, b and c represent relative atomic amounts of the elements, and when a=1, b=0.01 to 1.0 and c depends on the oxidation state of the elements other than oxygen. At flame temperatures, certain metal components of the mixed metal oxide catalyst volatilize leaving different mixed metal oxide catalysts, intermetallic catalysts and hybrid catalysts thereof.

(C) a catalyst comprising a mixed metal oxide having the empirical formula $$Mo_aSb_bBi_cO_d$$

wherein a, b, c and d represent relative atomic amounts of the elements, and when a=1, b=0.01 to 1.0, c=0.01 to 1.0 and d depends on the oxidation state of the elements other than oxygen. At flame temperatures, certain metal components of the mixed metal oxide catalyst volatilize leaving different mixed metal oxide catalysts, intermetallic catalysts and hybrid catalysts thereof.

Alternatively, the catalyst may comprise combinations of catalysts (A), (B) and (C).

Yet other alternative oxidation catalysts may comprise:

(a) a supported catalyst comprising at least one element selected from the group consisting of Groups 5B, 6B, 7B, and 8 of the periodic table of the elements promoted with at least one element selected from Group 1B of the periodic table of the elements plus bismuth oxide acetate; or
(b) a catalyst comprising ruthenium; or
(c) a catalyst comprising Pd and Bi on a support; or
(d) a supported catalyst comprising Pd and at least one element selected from the group consisting of elements of Groups 3A, 4A, 5A and 6B of the periodic table of the elements and at least one element selected from the group consisting of elements of Groups 3B and 4B of the periodic table of the elements; or
(e) a supported catalyst comprising Pd and at least one element of Group 1B of the periodic table of the elements; or
(f) a supported catalyst comprising Pd and Pb; or
(g) a supported catalyst comprising Pd and at least one element selected from the group consisting of Ba, Au, La, Nb, Ce, Zn, Pb, Ca, Sb, K, Cd, V and Te; or
(h) combinations thereof.

Another alternative catalyst comprises a phosphate catalyst containing Mo, V, Nb and/or Ta. (See Japanese Laid-Open Patent Application Publication No. 06-199731 A2.). Yet another alternative catalyst comprises any of the well-known molybdenum, bismuth, iron-based mixed metal oxides such as those disclosed in U.S. Pat. Nos. 3,825,600; 3,649,930 and 4,339,355.

The invention also provides a multi-stage process for the production of esters of unsaturated carboxylic acids, the process comprising the steps of:
(a) combining 5-30% by weight of a gaseous alkane, and a stoichiometric amount of molecular oxygen, fully oxidizing the alkane to carbon dioxide and water vapor in the form of steam;
(b) combining the steam and the remaining amount of alkane with the steam and carbon dioxide and directing it to contact one or more stem cracking catalysts; and
(c) converting the corresponding alkene generated from (b) and molecular oxygen to a short contact time reactor, the reactor including a mixed catalyst bed comprising (1) a first catalyst layer comprising (i) at least one metal selected from the group consisting of Ag, Au, Ir, Ni, Pd, Pt, Rh, Ru, alloys thereof and combinations thereof; and (ii) at least one modifier selected from the group of metal oxides including the metals Bi, In, Mg, P, Sb, Zr, Group 1-3 metals, lanthanide metals and combinations thereof, in combination with or without (iii) at least one metal oxide including the metals Cd, Co, Cr, Cu, Fe, Mn, Ni, Nb, Ta, V, Zn, binary combinations thereof, ternary combinations thereof and higher combinations thereof, wherein the catalysts of the first layer are impregnated on a metal oxide support; and (2) a second catalyst layer comprising at least one metal oxide including the metals Mo, Fe, P, V and combinations thereof, the mixed bed catalyst cumulatively effective at converting the gaseous alkane to its corresponding gaseous unsaturated carboxylic acid;
wherein the one or more cracking catalysts is separated at a distance upstream from the short contact time reactor;
wherein the second catalyst layer is separated at a distance downstream from the first catalyst layer and the reactor is operated at a temperature of from 500° C. to 1000° C., with a reactor residence time of no greater than 100 milliseconds.

According to one embodiment, an additional catalyst layer is included between the first and second layers comprising at least one metal oxide including the metals Mo, Fe, P, V and combinations thereof, the catalyst additional layer cumulatively effective at converting the gaseous saturated carboxylic acid to its corresponding gaseous unsaturated carboxylic acid before it is catalytically converted to its corresponding ester in the presence of an alcohol.

The invention also provides a multi-stage process for cumatively converting alkanes to their corresponding esters of unsaturated carboxylic acids, the reactor containing one or more oxidation catalysts cumulatively effective for converting the alkane to an ester of its corresponding unsaturated carboxylic acid with the alcohol; the one or more oxidation catalysts comprising a first catalyst system effective for converting the alkane to its corresponding unsaturated carboxylic acid and a second catalyst effective for converting the ethylenically unsaturated alcohol, in the presence of the alcohol, to an ester of its corresponding ethylenically unsaturated carboxylic acid with the alcohol;
the first catalyst being disposed in a first reaction zone;
the second catalyst being disposed in a second reaction zone;
the first reaction zone being disposed upstream of the second reaction zone relative to the direction of flow of the first gaseous stream through the reactor;
the second gaseous stream being fed to the reactor intermediate the first reaction zone and the second reaction zone;
the first reaction zone being operated at a temperature of from 500° C. to 1000° C., with a first reaction zone residence time of no greater than 100 milliseconds;
the second reaction zone being operated at a temperature of from 300° C. to 400° C., with a second reaction zone residence time of no greater than 100 milliseconds.

According to yet another embodiment, provides a multi-stage process for catalytically and cumulatively converting alkanes to their corresponding higher unsaturated carboxylic acids and then catalytically converting them to their corresponding esters in the presence of specific alcohols.

In preparing esters of ethylenically unsaturated carboxylic acids and higher analogues thereof using the multi-staged catalyst systems of the invention, it is useful to pass a first gaseous stream comprising propane or isobutane and molecular oxygen to the SCR to generate carbon dioxide and oxidize the remaining alkanes to corresponding alkenes propylene and isobutylene; to pass the corresponding alkenes to a SCTR with one or more oxidation catalysts to cumulatively convert the alkenes to corresponding unsaturated carboxylic acids and to separately pass a second gaseous stream comprising the alcohol to the reactor. In addition, the feed may contain an additional reactant, adjuvant such as steam or a diluent such as an inert gas, e.g., nitrogen, argon or additional oxidants including carbon dioxide. Any additional reactant feeds include but are not limited to alkenes, oxygen, air, hydrogen, carbon monoxide, carbon dioxide, and formaldehyde.

It is useful to pass, a first gaseous stream comprising propane or isobutane and molecular oxygen to the SCR then the corresponding alkene gaseous stream to the SCTR; and to separately pass a second gaseous stream comprising the alcohol and any additional feed to the SCTR. In addition, the feed may contain an adjuvant such as steam or a diluent such as an inert gas, e.g., nitrogen, argon or carbon dioxide.

Any source of molecular oxygen or other milder oxidants including carbon dioxide may be employed in this process, e.g., oxygen, oxygen-enriched gases or air. Air may be the most economical source of oxygen, especially in the absence of any recycle.

An alternative first catalyst may comprise a mixed metal oxide having the empirical formula $$Mo_aV_bM_cN_dQ_eX_fO_g$$

wherein

M is an element selected from the group consisting of Te and Sb,

N is at least one element selected from the group consisting of Nb, Ta, W, Ti, Al, Zr, Cr, Mn, B, In, As, Ge, Sn, Li, Na, K, Rb, Cs, Fr, Be, Mg, Ca, Sr, Ba, Hf and P, Q is at least one element selected from Group 8 of the periodic table of the elements, X is at least one element selected from the group consisting of Pb and Bi, a, b, c, d, e, f and g represent relative atomic amounts of the elements, and when $a=1$, $b=0.01$ to $1.0$, $c=0.01$ to $1.0$, $d=0.01$ to $1.0$, $e=0.001$ to $0.1$, $f=0.001$ to $0.1$ and g depends on the oxidation state of the elements other than oxygen. At flame temperatures, certain metal components, including Mo and Te, of the mixed metal oxide catalyst volatilize leaving different mixed metal oxide catalysts, intermetallic catalysts and hybrid catalysts thereof.

Another alternative first catalyst comprises a phosphate catalyst containing Mo, V, Nb and/or Ta. (See Japanese Laid-Open Patent Application Publication No.06-199731 A2.).

Yet another alternative first catalyst comprises a mixed metal oxide having the formula $P_aMo_bV_cBi_dX_eY_fZ_gO_h$, wherein X is As, Sb, Si, B, Ge or Te; Y is K, Cs, Rb, or Tl; Z is Cr, Mn, Fe, Co, Ni, Cu, Al, Ga, In, Sn, Zn, Ce, Y or W; a, b, c, d, e, f, g and h are the relative atomic amounts of the elements; and, when $b=12$, $0<a\leq3$, $c=0-3$, $0<d\leq3$, $0<e\leq3$, $f=0-3$, $g=0-3$, and h depends on the oxidation state of the other elements. (See Japanese Laid-Open Patent application Publication No. 09-020700 A2.).

Other alternative mixed metal oxide catalysts are usefully employed and have been described earlier in the specification.

The second catalyst is useful for catalyzing conversion of the ethylenically unsaturated carboxylic acid to its corresponding ester.

The second catalyst comprises a superacid. A superacid, according to the definition of Gillespie, is an acid that is stronger than 100% sulfuric acid, i.e. it has a Hammett acidity value $H_0<-12$. Representative superacids include, but are not limited to: zeolite supported $TiO_2/(SO_4)_2$, $(SO_4)_2/ZrO_2$—$TiO_2$, $(SO_4)_2/ZrO_2$—$Dy_2O_3$, $(SO_4)_2/TiO_2$, $(SO_4)_2/ZrO_2$—$NiO$, $SO_4/ZrO_2$, $SO_4/ZrO_2 Al_2O_3$, $(SO_4)_2/Fe_2O_3$, $(SO_4)_2/ZrO_2$, $C_4F_9SO_3H$—$SbF_5$, $CF_3SO_3H$—$SbF_5$, Pt/sulfated zirconium oxide, $HSO_3F$—$SO_2ClF$, $SbF_5$—$HSO_3F$—$SO_2ClF$, $MF_5/AlF_3$ (M=Ta, Nb, Sb), $B(OSO_2CF_3)_3$, $B(OSO_2CF_3)_3$—$CF_3SO_3H$, $SbF_5$—$SiO_2$—$Al_2O_3$, $SbF_5$—$TiO_2$—$SiO_2$ and $SbF_5$—$TiO_2$. Preferably, solid superacids are utilized, e.g., sulfated oxides, supported Lewis acids and supported liquid superacids. Only a small number of oxides produce superacid sites on sulfation, including $ZrO_2$, $TiO_2$, $HfO_2$, $Fe_2O_3$ and $SnO_2$. The acid sites are generated by treating an amorphous oxyhydrate of these elements with $H_2SO_4$ or $(NH_4)_2SO_4$ and calcining the products at temperatures of 500° C.-650° C. During the calcination, the oxides are transformed into a crystalline tetragonal phase, which is covered by a small number of sulfate groups. $H_2MoO_4$ or $H_2WO_4$ may also be used to activate the oxide.

Yet another alternative catalyst comprises any of the well-known molybdenum, bismuth, iron-based mixed metal oxides such as those disclosed in U.S. Pat. Nos. 3,825,600; 3,649,930 and 4,339,355.

In a separate embodiment, there is provided a multi-stage process for the production of esters of unsaturated carboxylic acids, the process comprising: passing a first gaseous stream comprising an alkane and molecular oxygen to a reactor; passing a second gaseous stream comprising an alcohol to the reactor; the reactor containing one or more oxidation catalysts cumulatively effective for the oxidation of the alkane to an ester of its corresponding unsaturated carboxylic acid with the alcohol; the one or more oxidation catalysts comprising a first catalyst effective for the oxidation of the alkane to its corresponding alkene, a second catalyst effective for the oxidation of the alkene to its corresponding unsaturated aldehyde, and a third catalyst effective for the oxidation of the unsaturated aldehyde, in the presence of the alcohol, to an ester of its corresponding unsaturated carboxylic acid with the alcohol; the first catalyst being disposed in a first reaction zone; the second catalyst being disposed in a second reaction zone; the third catalyst being disposed in a third reaction zone; the first reaction zone being disposed upstream of the second reaction zone relative to the direction of flow of the first gaseous stream through the reactor; the second reaction zone being disposed upstream of the third reaction zone relative to the direction of flow of the first gaseous stream through the reactor; the second gaseous stream being fed to the reactor intermediate the second reaction zone and the third reaction zone; the first reaction zone being operated at a temperature of from 500° C. to 900° C., with a first reaction zone residence time of no greater than 100 milliseconds; the second reaction zone being operated at a temperature of from 300° C. to 400° C., with a second reaction zone residence time of no greater than 100 milliseconds; the third reaction zone being operated at a temperature of from 100° C. to 300° C., with a third reaction zone residence time of no greater than 100 milliseconds.

In this aspect of the invention, it is useful to pass a first gaseous stream comprising propane or isobutane and molecular oxygen to the SCR and the corresponding alkene gaseous stream to the SCTR; and to separately pass a second gaseous stream comprising the alcohol to the SCTR. In addition, the feed may contain an adjuvant such as steam or a diluent such as an inert gas, e.g., nitrogen, argon or additional oxidants including carbon dioxide.

Any source of molecular oxygen or milder oxidants including carbon dioxide may be employed in this process, e.g., oxygen, oxygen-enriched gases or air. Air may be the most economical source of oxygen, especially in the absence of any recycle.

The appropriate catalyst is selected from respective catalysts described previously. Alternative catalyst components may comprise a reducible metal oxide promoted with a metal selected from Group 8 of the periodic table of the elements and supported on a three-dimensional support structure.

The support structure is three-dimensional, i.e. has dimensions along the x, y and z orthogonal axes of a Cartesian coordinate system, and affords a relatively high surface area per unit volume. Though lower and higher amounts are possible, in one embodiment, the support structure exhibits a surface area of 0.01 to 50 m²/g, preferably 0.1 to 10 m²/g.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above noted general criteria. Examples of suitable physical forms include foam, honeycomb, lattice, mesh, monolith, woven fiber, non-woven fiber, gauze, perforated substrates (e.g., foil), particle compacts, fibrous mat and mixtures thereof. For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses, as well as others.

The support structure may be fabricated from a material that is inert to the reaction environment of the catalytic reaction. Suitable materials include ceramics such as silica, alumina, silica-alumina, aluminosilicate, zirconia, titania, boria, mullite, lithium aluminum silicate, oxide-bonded silicon carbide or mixtures thereof. (Alternatively, the catalyst may be prepared so as to define the support structure itself, e.g., by "green" compacting or another suitable technique.)

The catalysts may be applied to the support structure using any suitable art-disclosed technique. For instance, the catalyst may be vapor deposited (e.g., by sputtering, plasma deposition or some other form of vapor deposition). The catalyst may be coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

The appropriate first catalyst is selected from catalysts described previously. Alternative first catalyst are also selected from catalysts described previously. Alternative first catalyst may be a binary, ternary, quaternary or higher order metal oxides. The reducible metal oxide may be an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof. Preferably, the reducible metal oxide is selected from the group consisting of Cu, Cr, V, Mn, Zn and mixtures thereof. The promoter is a metal from Group 8 of the periodic table of the elements (Fe, Ru, Os, Co, Rh, Ir, Ni, Pd and Pt), preferably a metal selected from the group consisting of Pt, Pd, Rh, Ir, Ru and mixtures thereof. The promoter may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

The appropriate second catalyst is selected from catalysts described previously. Alternative second catalysts may comprise any of the well-known molybdenum, bismuth, iron-based mixed metal oxides such as those disclosed in U.S. Pat. Nos. 3,825,600; 3,649,930 and 4,339,355.

The appropriate third catalyst is selected from catalysts described previously. The third catalyst comprises a superacid. A superacid, according to the definition of Gillespie, is an acid that is stronger than 100% sulfuric acid, i.e. it has a Hammett acidity value $H_0 < -12$. Representative superacids include, but are not limited to: zeolite supported $TiO_2/(SO_4)_2$, $(SO_4)_2/ZrO_2$—$TiO_2$, $(SO_4)_2/ZrO_2$—$Dy_2O_3$, $(SO_4)_2/TiO_2$, $(SO_4)_2/ZrO_2$—NiO, $SO_4/ZrO_2$, $SO_4/ZrO_2Al_2O_3$, $(SO_4)_2/Fe_2O_3$, $(SO_4)_2/ZrO_2$, $C_4F_9SO_3H$—$SbF_5$, $CF_3SO_3H$—$SbF_5$, Pt/sulfated zirconium oxide, $HSO_3F$—$SO_2ClF$, $SbF_5$—$HSO_3F$—$SO_2ClF$, $MF_5/AlF_3$ (M=Ta, Nb, Sb), $B(OSO_2CF_3)_3$, $B(OSO_2CF_3)_3$—$CF_3SO_3H$, $SbF_5$—$SiO_2$—$Al_2O_3$, $SbF_5$—$TiO_2$—$SiO_2$ and $SbF_5$—$TiO_2$. Preferably, solid superacids are utilized, e.g., sulfated oxides, supported Lewis acids and supported liquid superacids. Only a small number of oxides produce superacid sites on sulfation, including $ZrO_2$, $TiO_2$, $HfO_2$, $Fe_2O_3$ and $SnO_2$. The acid sites are generated by treating an amorphous oxyhydrate of these elements with $H_2SO_4$ or $(NH_4)_2SO_4$ and calcining the products at temperatures of 500° C.-650° C. During the calcination, the oxides are transformed into a crystalline tetragonal phase, which is covered by a small number of sulfate groups. $H_2MoO_4$ or $H_2WO_4$ may also be used to activate the oxide.

In a further separate embodiment of the invention, there is provided a process for the production of esters of unsaturated carboxylic acids, the process comprising: reacting an unsaturated aldehyde with an alcohol to form an acetal; passing a gaseous stream comprising the so-formed acetal and molecular oxygen to a reactor; the reactor containing at least one catalyst effective for the oxidation of the acetal to its corresponding ester; the reactor being operated at a temperature of from 300° C. to 1000° C., with reactor residence time of no greater than 100 milliseconds.

In a separate embodiment of the present invention, an alcohol is reacted with an unsaturated aldehyde to form an acetal. Such reaction can be carried out by contacting the aldehyde with an excess of the anhydrous alcohol in the presence of a small amount of an anhydrous acid, e.g., anhydrous HCl. Preferably, the aldehyde and the alcohol can be passed through a bed containing an acid catalyst, e.g., through a bed of a strongly acidic ion exchange resin, such as Amberlyst 15.

The so-formed acetal and molecular oxygen are fed to a reactor containing at least one catalyst effective for the oxidation of the acetal to its corresponding ester. Examples of such a catalyst include Pd and Bi on alumina or V oxides.

In this aspect of the invention, any source of molecular oxygen may be employed in this process, e.g., oxygen, oxygen-enriched gases or air. Air may be the most economical source of oxygen, especially in the absence of any recycle.

In a separate embodiment of this aspect of the invention, the unsaturated aldehyde is formed by oxidation of an alkane to its corresponding unsaturated aldehyde. This oxidation may be effected as a vapor phase oxidation of the alkane in the presence of a catalyst such as Pd and Bi on alumina or V oxides.

EXAMPLES

Comparative Example 1

Pt Impregnated on $Mo_aV_bM_cN_dQ_eX_fO_g$, Wash coated onto an Alumina Foam

An aqueous solution (200 mL) containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), oxalic acid (0.155M), palladium nitrate hydrate (0.01M Pd), and nitric acid (0.24M $HNO_3$) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The final catalyst had a nominal composition of $Mo_{1.0}V_{0.3}Te_{0.23}Nb_{0.17}Pd_{0.01}O_x$. 30 g of the catalyst were first treated with indium nitrate solution for one hour, followed by a drying and calcination steps mentioned above. This was followed by platinum coating step. The weights and the percent metals loadings are summarized in Table 1.

TABLE 1

Aluminum Foam-Platinum/Indium Oxides Catalysts.

| # | Ratio Pt/In | Support Weight (g)** | Catalyst Weight $1^{ST}$ application | % Loading | Catalyst Weight $2^{ND}$ application | % Loading |
|---|---|---|---|---|---|---|
| 1 | 10:1 | 1.827 | 1.872 | 2.46 | 1.900 | 3.99 |
| 2 | 3.3:1 | 1.901 | 1.947 | 2.41 | 1.981 | 4.21 |
| 3 | 2:1 | 1.708 | 1.787 | 4.63 | 1.821 | 6.62 |
| 4 | 1:1.78 | 1.748 | 1.806 | 3.32 | 1.822 | 4.23 |
| 4* | 1:1.78 | 1.757 | 1.958 | 11.43 | 1.971 | 12.58 |
| 5 | 1:5.4 | 1.682 | 1.749 | 3.98 | 1.749 | 11.83? |

*"Sequential procedure"
**Weight of three monoliths ground and added to 100 mL solution of 30% oxalic acid in water. The resulting suspension was stirred at 125° C. for 5 hrs in a Parr reactor, then the solids were collected by gravity filtration and dried in a vacuum oven overnight at 25° C.

The dried material from above, sized to ≦75 microns was impregnated by incipient wetness with an aqueous solution of platinic acid to result in a 0.01 molar loading of Pt with respect to Mo. The excess water was removed via a rotary evaporator at a temperature of 50° C. and a pressure of 28 mm Hg and then calcined in a quartz tube at 600° C. under an Ar flow of 100 cc/min for two hours. The resulting material was ground, sized to ≦75 microns, suspended in acetone (1 g/10 cc) and sonicated for 30 minutes. A 45 ppi alpha alumina foam (Vesuvius Hi-Tech of dimensions 12 mm diameter and 0.5 cm thickness) was dipped into the stirring catalyst/acetone suspension and then dried at room temperature under $N_2$ several times until no further weight gain was observed for the wash coated foam. Alternating sides of the foam were oriented for each cycle of wash coating which prevented clogging of foam's pores. The resulting wash coated foam weighed 0.112 g and consisted of 20 wt % catalyst.

Comparative Example 2

Pt/In Oxides Supported on α-alumina Foam Monoliths

Alpha-$Al_2O_3$ foam monoliths (45 pores per inch) were employed as supports in the preparation of two sets of catalysts. The first set comprises of six catalysts made with platinum and indium oxide of assorted ratios as specified in Table I. Five aqueous solutions of 8% $H_2PtCl_6$ (platinic acid) were spiked with various amounts of In $(NO_3)_3 \cdot 5H_2O$ to generate mixtures with platinum; niobium ratios specified in Table 1. These mixtures were kept with stirring at 40 c until homogeneous solutions were obtained (~30 min.). To each of the five mixtures three monoliths were added. The catalyst preparation was carried out by immersing the monoliths in the corresponding solutions at ambient temperature for one hour, followed by a drying step (100 c, 1 hr, N2), and finally, by a calcination step (600 c, 4 hr, air). This process was repeated twice (the "pearl" procedure). One catalyst from the above series (Pt:In=1:1.78) was prepared by a different method-the "sequential coating process". In this procedure, the monoliths were first treated with indium nitrate solution for one hour, followed by a drying and calcination steps mentioned above. This was followed by platinum coating step. The weights and the percent metals loadings are summarized in Table 1.

Comparative Example 3

Pt/Nb Oxides Supported on α-alumina Foam Monoliths

Alpha-$Al_2O_3$ foam monoliths (45 pores per inch) were employed as supports in the preparation of two sets of catalysts. The first set comprises of six catalysts made with platinum and indium oxide of assorted ratios as specified in Table 2. Five aqueous solutions of 8% $H_2PtCl_6$ (platinic acid) were spiked with various amounts of aqueous solution of ammonium niobium oxalate (0.17M Nb) to generate mixtures with platinum; niobium ratios specified in Table 1. These mixtures were kept with stirring at 40 c until homogeneous solutions were obtained (~30 min.). To each of the five mixtures three monoliths were added. The catalyst preparation was carried out by immersing the monoliths in the corresponding solutions at ambient temperature for one hour, followed by a drying step (100 c, 1 hr, N2), and finally, by a calcination step (600 c, 4 hr, air). This process was repeated twice (the "pearl" procedure). The results are summarized in Table 2.

TABLE 2

Aluminum Foam-Platinum/Niobium oxides catalysts.

| # | Ratio Pt/Nb | Support Weight (g)** | Catalyst Weight $1^{ST}$ application | % Loading | Catalyst Weight $2^{ND}$ application | % Loading |
|---|---|---|---|---|---|---|
| 1 | 10:1 | 2.080 | 2.107 | 1.30 | 2.126 | 2.21 |
| 2 | 10:3 | 1.824 | 1.842 | 0.98 | 1.871 | 2.58 |
| 3 | 1:1 | 1.855 | 1.884 | 1.56 | 1.907 | 2.91 |
| 4 | 1:3 | 1.852 | 1.891 | 2.11 | 1.901 | 2.65 |
| 5 | 1:10 | 1.762 | 1.791 | 1.65 | 1.820 | 3.30 |

Comparative Example 4

Pt/Nb/V Oxides Supported on α-alumina Foam Monoliths

Alpha-$Al_2O_3$ foam monoliths (45 pores per inch) were employed as supports in the preparation of Pd—Nb—V catalyst. A solution made of 8% Pd (palladium nitrate hydrate), 2% In (Indium nitrate hydrated), 0.4% V (ammonium metavanadate), oxalic acid (5 weight %) was kept with stirring at 40° C. Conc Nitric acid was added to generate a homogeneous solution of 2.0 pH. The catalyst preparation was carried out by immersing the monoliths in the corresponding solution at ambient temperature for one hour, followed by a drying step (100 c, 1 hr, N$_2$), and, finally, by a calcination step (600 c, 4 hr, air). This process was repeated twice resulted in 4.7% loading.

Comparative reactor data for propane conversion using the catalyst systems in a short contact time reactor (SCTR) of the invention are presented in Table 3.

TABLE 3

SCTR propane data for comparative catalyst systems of the invention

| Catalyst* | loading | Flow | Propane/ Oxygen | N2 (%) | preheat | Propane conversion (%) | Propylene yield (%) | Acrylic acid yield (%) | Propionic acid yield (%) |
|---|---|---|---|---|---|---|---|---|---|
| Pt/In | 10:1  | 2 | 1.4 | 15% | 200 | 64 | 21 | 0 | 0 |
| Pt/In | 3.3:1 | 2 | 1.4 | 15% | 200 | 73 | 19 | 0 | 0 |
| Pt/In | 2:1   | 2 | 1.4 | 15% | 200 | 73 | 18 | 0 | 0 |
| Pt/In | 1:5.4 | 2 | 1.4 | 15% | 200 | 81 | 15 | 0 | 0 |
| Pt/Nb | 10:1  | 2 | 1.4 | 15% | 200 | 59 | 19 | 0 | 0 |
| Pt/Nb | 3.3:1 | 2 | 1.4 | 15% | 200 | 49 | 15 | 0 | 0 |

*All catalysts were washcoated on a 45 ppi alpha-alumina foam, 5 mm long and 12 mm in diameter Table 4 summarizes physical properties of the molten salt method for preparing mixed metal oxide catalysts and catalyst systems.

TABLE 4

Selected Properties of Metal Halides

| Niobium | | Vanadium | | Tellurium | | Molybdenum | |
|---|---|---|---|---|---|---|---|
| Salt | mp (° C.) | Salt | mp (° C.) | Salt | mp (° C.) | Salt | mp (° C.) |
| NbBr5 | 265 |      |       | TeBr2 | 210 |       |     |
| NbCl5 | 205 | VCl4 | −25.7 | TeCl4 | 224 | MoCl5 | 194 |
| NbF5  | 72  |      |       |       |     |       |     |

Multi-Staged Catalyst System Example 1

The first catalyst uses propane as fuel with molecular oxygen to generate a milder oxidant, carbon dioxide and steam, which reduces the temperature of the conversion to propane to propylene at short contact time. The amount of propane sacrificed as fuel and to generate carbon dioxide is sufficient (5 to 30% by weight) to generate the amount of heat needed for the second catalytic stage, the catalytic dehydrogenation of propane to propylene. An exemplary first catalyst comprises a metal selected from Group 8, Pt, Rh, Pd, Ir in the form of a gauze, mesh, wires and combinations thereof. The catalysts is unsupported or is supported on a three-dimensional structure including a foam, monolith, coated channel or microreactor that is selected from silica, alumina, silicates, aluminosilicates and zeolites. The reaction is conducted at contact times on the order of milliseconds and at temperatures greater than 700° C.

The exotherm generated from the full propane oxidation is used to provide heat for the endothermic dehydrogenation of propane to propylene under steam cracking conditions. In addition any hydrogen generated is used as fuel for the conversion of alkane to its corresponding alkene. Another advantage to the invention is from use of hyrdrogen as a fuel in the conversion, consistent with work on C2 conversions reported by L. Schmidt et al. The steam cracking catalysts comprises an activated zeolite, ZSM-5, that has been ion exchanged or framework substituted to optimize it cracking efficiency. In Superflex technology it has been reported that incorporation of phosphorus into ZSM-5 improves the FCC performance at residence times on the order of a second. The reaction is carried out under short contact times and temperatures greater than 500 C. The effluent from the short contact time is directed to a third stage or catalytic structure for selective oxidation. It is also useful at this stage to add one or more additional oxidants selected from air, oxygen, carbon dioxide and nitrous oxide, including additional steam. Useful or desirable oxygenates produced include acrylic acid, acrolein, acrylic acid esters, methacrylic acid and methacrylic acid esters. Esters require additional staging for alcohols and higher analogues also require appropriate additional staging. The selective oxidations are carried out at temperatures above 300° C. Mixed metal oxide catalysts are useful.

The multi-staged catalysts are situated in a tubular reactor in series with the appropriate catalysts staging as described. Additional heat may be supplied to the second and third stage catalytic zones as needed to achieve useful conversion yields. Integrated catalytic zones are also usefully employed that are thermally integrated for optimized nergy balances. The structure may comprise an effective heat exchange material including alloys of Fe—Cr—Al-oxides. The catalysts may be supported on alumina monoliths. Other types of staged catalysts are also usefully employed.

Multi-Staged Catalyst System Example 2

Isobutane was catalytically converted to methacrylic acid at short contact times using a Pt/Na—[Fe]-ZSM-5 type. This catalyst has been demonstrated to exhibit high selectivity by L. Schmidt et al. in the conversion of propane to propylene in conventional oxidative dehydrogenation. Addition of low levels of Pt will make the catalyst suitable for flame temperatures in a SCTR. Incorporation of phosphorus into ZSM-5 is expected to further improve selectivity and yield at constant alkane conversion. The effluent gaseous stream is directed to a second catalytic zone for selective oxidation. It is also useful at this stage to add one or more additional oxidants selected from air, oxygen, carbon dioxide and nitrous oxide, including additional steam and fuel in the form of oxidized hydrogen. In addition any hydrogen generated is used as fuel for the conversion of alkane to its corresponding alkene. Another advantage to the invention is from use of hydrogen as a fuel in the conversion, consistent with work on C2 conversions reported by L. Schmidt et al. Useful or desirable oxygenates produced include methacrylic acid and methacrylic acid esters. Esters require additional staging for alcohols and higher analogues also require appropriate additional staging. The selective oxidations are carried out at temperatures above 300° C. Mixed metal oxide catalysts are useful.

What is claimed:

1. A multi-stage method for preparing $C_3$-$C_8$ alkenes from corresponding $C_3$-$C_8$ alkanes, comprising the steps of:
   (A) combining 5-30% by weight of a $C_3$-$C_8$ alkane, and a stoichiometric amount of molecular oxygen, fully oxidizing the alkane to produce carbon dioxide, water vapor, and unreacted alkane;
   (B) combining the carbon dioxide, water vapor, and unreacted alkane to form a combined feed stream; and
   (C) contacting the combined feed stream with one or more steam cracking catalysts at a temperature of from 700° C. to 1000° C. and a residence time of no greater than 100 milliseconds, to produce the corresponding $C_3$-$C_8$ alkene,
   wherein the one or more steam cracking catalysts comprise a catalyst system cumulatively effective at converting the $C_3$-$C_8$ alkane to its corresponding $C_3$-$C_8$ alkene and comprising: (1) at least one metal selected from the group consisting of: Ag, Au, Ir, Ni, Pd, Pt, Rh, Ru, alloys thereof and combinations thereof; and (2) at least one modifier selected from the group of metal oxides including the metals Bi, In, Mg, P, Sb, Zr, Group 1-3 metals, lanthanide metals and combinations thereof,
   wherein the one or more steam cracking catalysts further comprise (3) at least one oxide of a metal selected from the group consisting of: Cd, Co, Cr, Cu, Fe, Mn, Ni, Nb, Ta, V, Zn, and combinations thereof.

2. A multi-stage method for cumulatively converting $C_3$-$C_8$ alkanes to their corresponding $C_3$-$C_8$ oxygenates, comprising the steps of:
   (A) performing the multi-stage method for preparing $C_3$-$C_8$ alkenes from corresponding $C_3$-$C_8$ alkanes according to claim 1, wherein the corresponding $C_3$-$C_8$ alkene is produced; and
   (B) contacting the corresponding $C_3$-$C_8$ alkene with at least one selective oxidation catalyst comprising at least one metal oxide including the metals Mo, Fe, P, V and combinations thereof, to produce at least one corresponding $C_3$-$C_8$ oxygenate selected from the group consisting of: carboxylic acids and esters thereof.

3. The multi-stage method according to claim 2, wherein the selective oxidation catalyst is separated at a distance downstream from the cracking catalyst.

* * * * *